(12) United States Patent
Steynberg

(10) Patent No.: US 6,974,844 B2
(45) Date of Patent: Dec. 13, 2005

(54) PROCESS FOR STARTING UP A FISCHER-TROPSCH REACTOR

(75) Inventor: André Peter Steynberg, Vanderbijlpark (ZA)

(73) Assignee: Sasol Technology (Proprietary) Limited, Johannesburg (ZA)

(*) Notice: Subject to any disclaimer, the term of this patent is extended or adjusted under 35 U.S.C. 154(b) by 0 days.

(21) Appl. No.: 10/915,253

(22) Filed: Aug. 10, 2004

(65) Prior Publication Data

US 2005/0027020 A1 Feb. 3, 2005

Related U.S. Application Data

(63) Continuation of application No. PCT/IB03/00450, filed on Feb. 12, 2003.

(30) Foreign Application Priority Data

Feb. 13, 2002 (ZA) .................................. 2002/1224

(51) Int. Cl.$^7$ ............................................. C07C 27/00
(52) U.S. Cl. ........................ 518/712; 518/705; 518/728
(58) Field of Search ............................... 518/712, 705, 518/728

(56) References Cited

U.S. PATENT DOCUMENTS

| 4,626,552 | A | 12/1986 | Arcuri |
| 5,389,690 | A | 2/1995 | Mitchell |
| 5,780,381 | A | 7/1998 | Wilson et al. |
| 6,512,017 | B1 | 1/2003 | Steynberg et al. |

FOREIGN PATENT DOCUMENTS

FR 1 004 318 3/1952

*Primary Examiner*—J. Parsa
(74) *Attorney, Agent, or Firm*—Ladas & Parry LLP

(57) ABSTRACT

A process for starting up a Fischer-Tropsch reactor includes establishing, in the reactor, an initial charge of molten wax. The initial reactor temperature is below the line-out reactor temperature but is sufficiently high for a Fischer-Tropsch reaction to take place. The reactor contains, in contact with the molten wax, at least a portion of its line-out catalyst inventory. Syngas is fed into the reactor at an initial flow rate below the line-out syngas flow rate. Initially a syngas $H_2:CO$ molar ratio is maintained at a higher value than its line-out value, whereafter the syngas $H_2:CO$ molar ratio is decreased to its line-out value. The syngas flow rate and the reactor temperature are then increased to their line-out values.

16 Claims, 1 Drawing Sheet

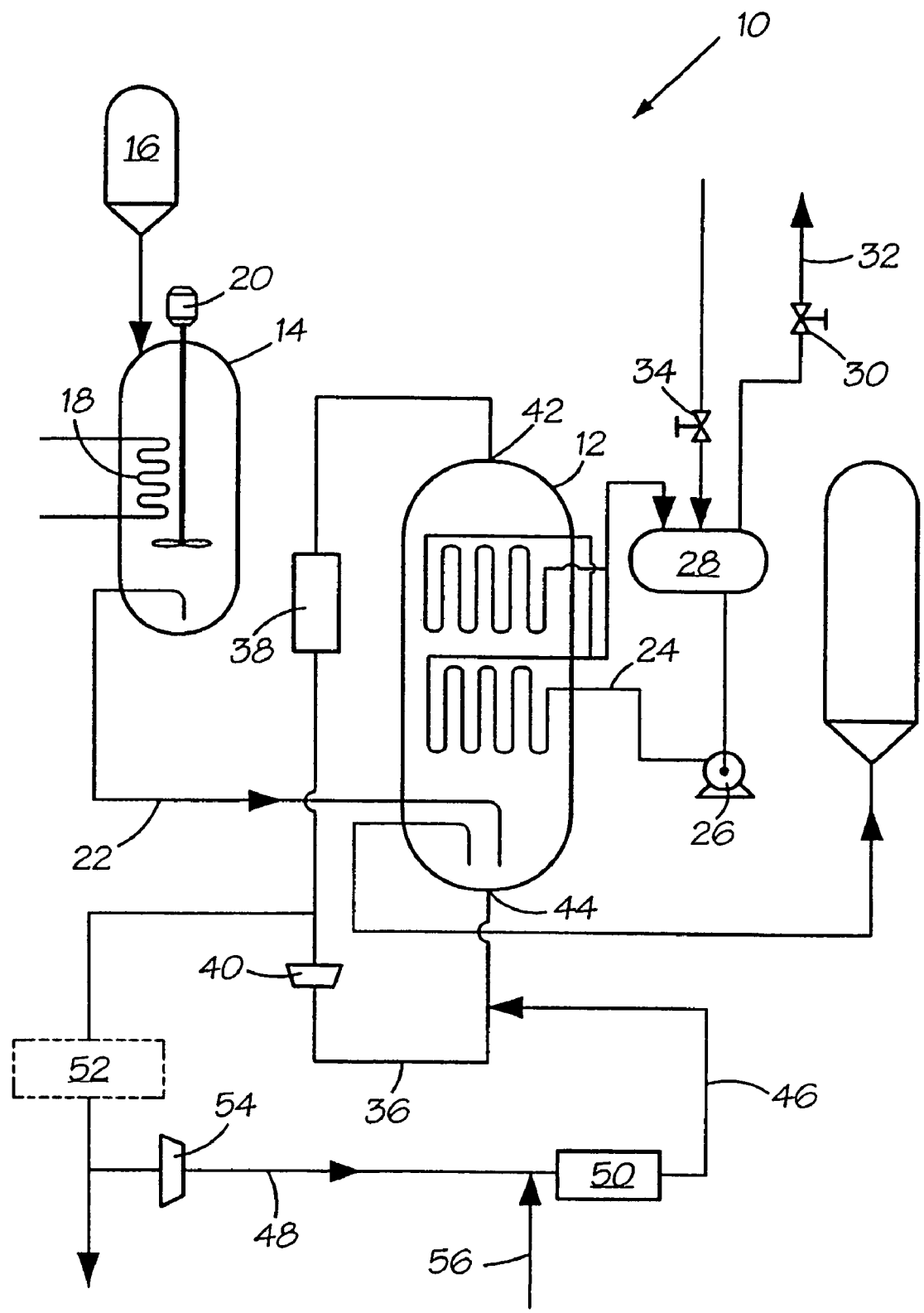

PROCESS FOR STARTING UP A FISCHER-TROPSCH REACTOR

This application is a continuation of copending International Application PCT/IB03/00450 filed on 12 Feb. 2003, which designated the U.S., claims the benefit thereof and incorporates the same by reference.

THIS INVENTION relates to a process for starting up a Fischer-Tropsch reactor.

The Applicant is aware of a reactor which, in use and at line-out conditions, contains a bed of a particulate Fischer-Tropsch catalyst, with a synthesis gas (hereinafter also referred to as 'syngas') which consists mainly of CO and $H_2$, being reacted in the reactor in the presence of the Fischer-Tropsch catalyst, and under Fischer-Tropsch reaction conditions, to produce hydrocarbon products. Such a reactor is hereinafter also referred to as a 'Fischer-Tropsch reactor'.

Syngas may be obtained from natural gas, comprising mainly methane, that is reformed in a reforming stage, which may comprise one or more of a steam reformer, a partial oxidation reformer, and an auto-thermal reformer.

During operation of the Fischer-Tropsch reactor, the syngas $H_2$:CO molar ratio is controlled in a preferred range, typically between 1:1 and 2:1. In other words, the line-out value of the $H_2$:CO molar ratio is controlled at between 1:1 and 2:1. This control is usually achieved by the recycle of tail gas from the Fischer-Tropsch reactor, or of components derived from the tail gas, to the reforming stage.

The Fischer-Tropsch reaction is an exothermic reaction and requires means for heat removal and thermal control. Heat removal and thermal control is managed by internal cooling means inside the reactor. Temperature control in a Fischer-Tropsch reactor is important for good catalyst management, particularly during start-up. For example, in a slurry phase Fischer-Tropsch reactor, catalyst degradation, ie catalyst damage and/or catalyst deactivation, can result if there is poor temperature control during start-up, eg if a temperature runaway occurs. It is thus an object of this invention to provide an improved process for starting up a Fischer-Tropsch reactor, whereby this problem is at least alleviated.

Therefore, according to the invention, there is provided a process for starting up a Fischer-Tropsch reactor, which process includes:

establishing, in a Fischer-Tropsch reactor, an initial charge of molten wax, with an initial reactor temperature which is below the line-out reactor temperature but sufficiently high for a Fischer-Tropsch reaction to take place, and with the reactor containing, in contact with the molten wax, at least a portion of its line-out catalyst inventory;

feeding syngas into the reactor at an initial flow rate below the line-out syngas flow rate;

initially maintaining a syngas $H_2$:CO molar ratio at a higher value than its line-out value;

thereafter decreasing the syngas $H_2$:CO molar ratio to its line-out value; and increasing the syngas flow rate and the reactor temperature to their line-out values.

While the Fischer-Tropsch reactor can, at least in principle, be a fixed bed reactor, it is envisaged that the invention will, in particular, apply to a slurry phase Fischer-Tropsch reactor in which, at line-out conditions, the catalyst inventory is contained in a slurry bed of particles of the catalyst in suspension in molten wax.

The Fischer-Tropsch catalyst may then, in particular, be a supported cobalt catalyst.

Fischer-Tropsch reactors thus normally have at least two phases of operation, namely a start-up phase and a line-out phase which follows on the start-up phase. During the start-up phase, initial or start-up reactor temperatures, syngas flow rates and syngas $H_2$:CO molar ratios are maintained. The start-up phase normally has a limited duration, and the line-out phase follows once the reactor temperatures, syngas flow rates and syngas $H_2$:CO molar ratios have been established at their long-term more-or-less steady state values. Thus, the line-out phase normally is of substantially longer duration than the start-up phase, and endures until it becomes necessary to shut the reactor down. The catalyst inventory or line-out catalyst inventory of a Fischer-Tropsch reactor is thus the entire loading of catalyst contained within the reactor once it has attained line-out conditions.

As indicated hereinbefore, the line-out value of the syngas $H_2$:CO molar ratio is typically controlled at between 1:1 and 2:1. It is thus controlled at less than the consumption ratio thereof during the Fischer-Tropsch synthesis in the reactor. During start-up, ie initially, the syngas $H_2$:CO molar ratio will thus be maintained at a value higher than 2:1, and which can be as high as 2.5:1. However, typically, it will be controlled at a value between about 2.1:1 and 2.4:1 during start-up.

The syngas may, in particular, be that obtained by reforming natural gas in a reforming stage ahead of the Fischer-Tropsch reactor. The decrease in the syngas $H_2$:CO molar ratio may then be effected by recycling carbon dioxide-containing gas to the reforming stage. In particular, the carbon dioxide-containing gas that is recycled to the reforming stage may be a tail gas from the Fischer-Tropsch reactor. The process can then, ie when the tail gas recycle is present, be said to employ an external recycle system. Thus, the syngas that is fed into the reactor may, in particular, comprise reformed natural gas and reformed external recycle gas.

The initial reactor temperature may be between 180° C. and 200° C., while the line-out reactor temperature may be between 220° C. and 260° C.

The initial syngas flow rate may be from 30% to 70% of its line-out value.

The process may, in particular, include initially providing in the reactor, ie when the initial reactor temperature and the initial syngas flow rate prevail, a partial catalyst inventory. The partial catalyst inventory may typically comprise between 5% and 50% of the line-out catalyst inventory. The process may then include, once the syngas $H_2$:CO molar ratio is at, or at least close to, its line-out value, adding further catalyst to the reactor to make up the line-out catalyst inventory.

In a particular embodiment of the invention, the process may include:

initially establishing, in the reactor, a charge of molten clean wax containing substantially no catalyst particles;

maintaining the charge of molten clean wax at a temperature above 150° C. and below 180° C.;

providing a slurry of molten wax and catalyst particles in a loading vessel;

transferring the slurry of molten wax and catalyst particles from the loading vessel to the reactor, where it is mixed with the charge of molten clean wax; and thereafter raising the temperature in the reactor to the initial reactor temperature.

The clean molten wax may typically be at a temperature of about 160° C.

The process may then, ie while the reactor contains the charge of molten clean wax, include recycling syngas that has passed through the reactor, after cooling and compression thereof, to the reactor, with the recycled syngas thus constituting an internal recycle. It will be appreciated that the syngas then passes through the reactor in substantially unreacted form since the reactor temperature is below 180° C. and since the reactor contains no catalyst. Thus, substantially no external syngas then enters the reactor. The internal recycle flow rate will typically be at the maximum rate that the internal recycle compressor can deliver.

The Fischer-Tropsch catalyst that is used in the Fischer-Tropsch reactor is typically protected during transport and storage thereof by being in the form of wax-coated particles. In other words, the catalyst is provided in the form of discrete wax pieces each containing a plurality of catalyst particles.

The slurry in the loading vessel may then be prepared by adding the wax-coated catalyst particles to the loading vessel, and thereafter heating the loading vessel to melt the wax and form the slurry of catalyst and molten wax. Alternatively, the wax coated catalyst may be melted in a separate vessel prior to transfer thereof to the loading vessel.

The loading vessel is preferably pressurized to a pressure of about 200 kPa above that of the pressure in the Fischer-Tropsch reactor, so that the slurry is transferred from the loading vessel to the Fischer-Tropsch reactor by pressure differential, with a transfer pump thus not being required. Typically, the loading vessel is pressurized to a pressure of 1000 kPa to 5000 kPa, generally about 2600 kPa.

The loading vessel may be heated to a temperature above 150° C. before the pressure within the loading vessel is increased to above 100 kPa using a gas containing carbon monoxide.

The entire partial catalyst inventory may be added to the reactor while syngas is recycled therethrough by means of the internal recycle, and while the reactor temperature is below the temperature at which the Fischer-Tropsch reactor is initiated, eg is 180° C. As hereinbefore set out, the partial catalyst inventory may comprise less than 50%, typically about 25%, of the total quantity of catalyst to be loaded, ie the catalyst inventory at line-out conditions.

The catalyst may be added in increments of, for example, about 5% until the entire partial catalyst inventory has been reached. The slurry of catalyst in wax may comprise up to 70% by mass catalyst, typically from 40% to 50% by mass, during transfer, based on the total slurry mass.

The temperature within the reactor is thus maintained below 180° C. until the about 25% of the desired catalyst loading or inventory is reached, whereafter additional syngas is introduced and the temperature increased to a temperature at which the Fischer-Tropsch reaction takes place, ie to about 180° C. to 200° C.

Preferably, the flow rate of the syngas in the internal recycle system is sufficient to fully fluidize the catalyst in the slurry in the reactor, prior to the initiation of the Fischer-Tropsch reaction.

It will be appreciated that the abovementioned procedure can also be used when restarting the reactor after it has been shut down by stopping the syngas flow to the reactor, while operating an internal recycle system; cooling the reactor to between 150° C. and 200° C. while the internal recycle system continues to operate; and transferring slurry from the reactor to an unloading vessel while continuing to operate the internal recycle system. In restarting the reactor, the slurry is then reloaded into the emptied reactor from the loading vessel, and the reactor restarted in the manner hereinbefore described.

Similarly, the procedure hereinbefore described may be employed after dealing with a failure of the external recycle system of the reactor, ie a recycle system comprising the recycle of tail gas from the reactor to the reforming section, by stopping the supply of syngas, maintaining an internal recycle system as hereinbefore described, lowering the temperature of the reactor to below 200° C. and unloading at least a portion of the catalyst from the reactor to an unloading vessel, with the restarting of the reactor being effected by introducing syngas flow into the reactor and then increasing the temperature of the reactor to about 230° C.; and reloading the unloaded catalyst from the unloading vessel via a loading vessel to the reactor, in the manner hereinbefore described.

Also in similar fashion, the procedure hereinbefore described may be employed after failure of an internal recycle system of the reactor has been dealt with by stopping syngas flow to the reactor, adding a quenching agent to cool the rector while optionally simultaneously decreasing the pressure in the reactor, maintaining the temperature in the reactor between 150° C. and 200° C. by controlling the temperature of the water that is pumped through cooling pipes in the reactor, and optionally unloading at least a portion of the catalyst from the reactor to an unloading vessel. The restarting of the reactor may then be effected by restarting the internal recycle system; if necessary, pressurizing the reactor to the normal operating pressure of between 800 kPa to 4800 kPa, typically about 2400 kPa; heating the reactor by pumping heating fluid through the cooling pipes of the reactor; and thereafter carrying out the steps hereinbefore described for starting up a Fischer-Tropsch reactor.

The invention will now be described in more detail with reference to the accompanying flow diagram of a process which includes a Fischer-Tropsch reactor, and in which a process for starting up the Fischer-Tropsch reactor, in accordance with the invention, can be carried out.

In the drawing, reference numeral 10 generally indicates a process which includes a slurry phase Fischer-Tropsch reactor 12. The reactor 12 contains a slurry bed (not shown) of Fischer-Tropsch catalyst particles suspended in molten wax.

Due to the long life of Fischer-Tropsch catalysts and the relatively large quantities required, the catalyst is usually prepared at a separate location to the slurry phase reactor 12 and stored for relatively long periods before it is used in the reactor.

In order to protect the catalyst from oxidation during storage and transportation, it is coated with a solid wax, for example SASOL Paraflint™ H1 hydrogenated hard wax. The coated catalyst is prepared by melting the wax, adding the catalyst particles in an inert gas environment (ie free of oxygen), and allowing the catalyst/wax mixture to cool and harden. The catalyst/wax mixture is preferably formed into discrete pieces of solid wax each containing a plurality of particles of catalyst embedded therein. Such discrete wax pieces are convenient to handle. The solid wax pieces are preferably in the form of cylindrical blocks, which can be stored in drums. The wax protects the catalyst particles embedded therein from oxidation.

A wax slurry containing catalyst particles is introduced into the Fischer-Tropsch reactor 12 via a loading vessel 14. Coated catalyst wax pieces (not shown) are added to the loading vessel 14 via a size reduction device for example a rotary crusher, a lock hopper or small scale melting vessel 16. The loading vessel 14 is a pressure vessel containing heating pipes 18 and a mixer 20. The heating medium within the heating pipes 18 is steam at a pressure of about 12 bar (g) (1200 kPa). The loading vessel 14 is pressurized with a gas that is practically free of sulphur or any oxidizing gas such as oxygen or water vapour. A convenient gas to use is compressed nitrogen, syngas or tail gas from a slurry phase reactor. The loading vessel 14 is heated, by the heating pipes 18, to a temperature above 150° C. before the pressure is increased to above 1 bar (g) (100 kPa), to avoid the formation of cobalt carbonyl when a cobalt catalyst is used. The wax which coats the catalyst particles melts as the loading vessel 14 heats up, so that a wax slurry containing catalyst particles is thereby formed in the loading vessel 14. After the catalyst/wax slurry is heated above 150° C., the pressure in the loading vessel 14 is increased to about 2 bar (200 kPa) above the pressure in the slurry phase reactor 12, generally to a pressure of about 26 bar (g) (2600 kPa).

The loading vessel 14 is arranged to load the slurry of molten wax and catalyst via a pipe 22 into the slurry phase reactor 12.

Before adding the wax and catalyst to the slurry phase reactor 12, a clean wax, ie a wax containing little or no catalyst, is introduced into the reactor 30. The amount of clean wax added is sufficient to submerge the internal components of the reactor 12, once molten. The clean wax is then heated in the reactor to a temperature above 150° C., typically about 160° C. The slurry phase reactor 12 contains pipes 24, typically at more than one elevation, that are normally used for cooling the reactor. These same pipes are used in the start-up procedure to heat the reactor to the temperature above 150° C. The pipes 24 are heated with steam from a high pressure steam header 26 that is at sufficient pressure to maintain a temperature in a steam drum 28 connected to the pipe 24, above 210° C. and preferably above 230° C. During normal operation the water/steam is passed in a two-phase flow through the pipes 24 into the steam drum 28 where further water vapour is flashed off and the resulting steam is discharged through a pressure control valve 30 into a medium pressure steam header 32. The steam header 32 may operate at any pressure between about 6 and 16 atmospheres (600 and 1600 kPa) but the pressure is typically about 12 bar (g) (1200 kPa). During the heating mode the steam drum pressure control valve 30 to this medium pressure steam header 32 is closed and pressure within the steam drum 28 is controlled by a separate control valve 34 that introduces steam from a high pressure steam source via a conduit and optionally a sparger (submerged in the water phase in the steam drum).

The reactor 12 is connected to an internal recycle system 36 (shown by a continuous line) which includes a cooling and liquid separation stage 38 and is driven by a compressor 40. The internal recycle system 36 exits the reactor 12 at a reactor outlet 42 and enters the reactor 12 at a reactor inlet 44. The reactor 12 and internal recycle system 36 are charged with syngas which is recycled via the internal recycle system 36 through the molten wax in the reactor 12.

Once the reactor 12 has reached a temperature of 160° C. and a pressure at or below the normal operating pressure of about 24 bar (g) (2400 kPa), with the recycled syngas being introduced via the internal recycle system 36 at a flow rate of at least 5 cm/s, wax slurry containing catalyst from the loading vessel 14 is transferred to the reactor 12. Because the pressure in the loading vessel 14 is higher than the pressure in the reactor 12, the slurry containing the catalyst is transferred to the reactor without the need to use a pump.

The quantity of catalyst introduced into the reactor 12, while the reactor is connected to the internal recycle system 36 only, is less than the total quantity to be loaded for normal or line-out operation. Less than 50%, typically about 25%, of the normal or line-out catalyst inventory is thus introduced, as a partial catalyst inventory. The catalyst content of the slurry transferred from the loading vessel 14 may be up to 70% by mass but is typically between 40 and 50% by mass of the slurry composition.

The catalyst which is introduced while the internal recycle system 36 only is running, may be introduced all at once, or it may be introduced incrementally. For example, where a partial catalyst inventory of 25% of the total or line-out catalyst inventory is introduced, catalyst may be introduced in two separate steps of 12.5% catalyst or five separate steps of 5%.

After 25% of the catalyst has been introduced, and ensuring that the reactor internals are submerged in molten wax, the temperature within the reactor 12 is brought up to about 180° C. to 200° C., at which temperature the Fischer-Tropsch reaction is initiated. The internal recycle flow rate is maintained at as high a flow rate as possible given that the compressor is designed for line-out conditions.

The temperature of the slurry within the reactor 12 is controlled by manipulating the temperature of the water through the pipes 24, bearing in mind that a Fischer-Tropsch reaction that generates heat will have already started. The reactor 12 is then connected to a source of syngas 46. The syngas 46 comprises a product gas from a reformer unit 50. The reformer unit 50 is supplied with natural gas 56 which it converts to fresh syngas. The syngas 46 flow rate is typically kept below the line-out syngas flow rate. The syngas $H_2$:CO molar ratio is determined, inter alia, by the flow rate of an external tail gas recycle 48, to a value which is higher than its line-out value. For example, it may be maintained at a value of about 2.1:1. The external recycle 48 includes an optional processing stage 52 and a compressor 54.

The temperature of the reactor 12 is then brought up to its normal or line-out operating temperature of 230° C. The syngas flow rate is then increased to its normal or line-out value. After establishing the normal operating temperature of 230° C. and while establishing the line-out syngas flow, the external recycle 48 flow rate is set to control the syngas $H_2$:CO molar ratio to the normal or line-out operating range between 1.90 and 1.95. The remainder of the catalyst is then added from the loading vessel at full Fischer-Tropsch reactor operating conditions.

In the above start-up procedure it is preferable to maintain the temperature of the slurry within the reactor 12 below 200° C. until the external recycle loop 48 has been established, whereafter the temperature is gradually increased to the 230° C. normal operating value. Typically, the gas loop composition is allowed to stabilize after each 5° C. increase in reactor operating temperature, and the syngas flow is at 30% to 70% of the normal operating rate.

The reasons for the abovementioned method are as follows:

Clean wax is introduced into the reactor before introducing the catalyst to avoid significant periods during which the catalyst is contacted with carbon monoxide within the reactor at temperatures below 150° C. which could lead to the formation of cobalt carbonyls.

When new catalyst is introduced into a reactor it has a much higher initial activity than the eventual stable activity that is maintained for several years. The catalyst may be damaged if any of the following events occur:

a) the partial pressure of water in the reactor exceeds about 5 bar (500 kPa);

b) the partial pressure of carbon monoxide decreases to below 0.5 bar (50 kPa); or c) the temperature of the catalyst slurry exceeds 240° C.

During normal operation the syngas $H_2$:CO ratio is controlled by adjusting the flow rate of tail gas recycle to the auto-thermal reformer (external recycle).

With the external recycle system operating during normal operation, it is not possible to exceed the constraints in a) and b), even at 100% of the conversion of hydrogen entering the Fischer-Tropsch in the syngas. This is due to $H_2$:CO ratio being below the stoichiometric consumption ratio so that the CO remaining cannot decrease to a partial pressure below 0.5 bar (50 kPa) from constraint b). The procedures described previously are required to avoid constraints a), b) and c) during the start-up before a stable syngas composition is attained.

For constraint a) it may be noted that gas from the reactor outlet 42 is cooled to typically about 70° C., or less to condense water vapour before it is recycled as internal recycle to the reactor feed conduit. The dry recycle gas flow can therefore be set to avoid exceeding the water partial pressure constraint. A further requirement for the recycled gas flow is that it should be sufficient to fully fluidize the catalyst in the absence of syngas. As a result of reaction with syngas any zones of stagnant catalyst can cause local high temperatures exceeding 240° C. It has been found that the minimum velocity needed to fluidize all the catalyst may be as high as about 15 cm/s for a slurry phase reactor containing supported cobalt catalyst with a maximum particle size of 200 microns. Thus, the catalyst is fully fluidized with recycled gas prior to the introduction of syngas.

EXAMPLE

Conditions prior to start-up of the Fischer-Tropsch slurry phase reactor are as follows:

a) Autothermal reformer 50 operating with 0.6 steam to reformable carbon ratio with recycle of syngas to the reformer inlet to achieve a syngas $H_2$:CO ratio of less than 2.2:1.

b) Autothermal reformer 50 typically operating at 30% to 70% of design capacity.

c) The slurry phase reactor 12 is pressurised to the normal operating pressure with this syngas and the internal recycle compressor 40 is started. The internal recycle 36 flow rate is maintained at maximum capacity.

d) Clean wax is transferred to the reactor prior to or soon after step (c) to establish the minimum operating level required to submerge all the reactor internals.

e) Solid catalyst/wax pieces are loaded into the melting and loading vessel 14 via the lock hopper 16. As the pieces heat up, the wax melts so that a molten wax/catalyst particle slurry is formed; this molten slurry is heated to above 150° C. and then prepared for transfer to the reactor by increasing the pressure in the melting and loading vessel to approximately 2 bar (200 kPa) above the pressure in the reactor using external recycle gas (not shown).

f) The water in the steam drum 28 is heated to approximately 260° C. by introducing high pressure steam and this hot water is circulated through the pipes in the reactor to heat the wax to a temperature of about 180° C., which is below the normal or line-out reactor operating temperature.

The reactor start-up then proceeds as follows:

a) Transfer catalyst/wax slurry (12.5% of the total catalyst inventory) to the reactor.

b) Melt the next 12.5% of the wax coated catalyst while simultaneously removing wax from the reactor by filtration to decrease the level to the minimum operating level.

c) Transfer the catalyst/wax slurry to the reactor.

d) Maintain the internal recycle flow rate at maximum capacity.

e) Establish a syngas flow 46 comprising reformed natural gas 56 and external recycle 48. The syngas flow rate is maintained at about 50% of its line-out value.

f) Maintain the syngas $H_2$:CO molar ratio at about 2.1:1, ie at a value which is higher than its line-out value, by using the maximum external recycle compressor capacity.

g) Allow the reactor temperature to increase to above 200° C. and then shut the high pressure steam and decrease the steam drum pressure by venting steam to the medium pressure steam header 26. This decreases the temperature of the water to below the temperature of the slurry inside the reactor. Heat is thus removed from the reactor as the exothermic Fischer-Tropsch reaction proceeds in order to control the slurry temperature. The temperature control set point is gradually increased (say 5° C. every 30 minutes) in order to increase the reactor temperature from 200° C. to the 230° C. normal or line-out operating temperature.

h) During the temperature increase period the tail gas (ie gas that exits reactor outlet 42) composition, and hence the external recycle 48 composition, changes. After establishing the normal or line-out operating temperature and syngas flow rate it becomes possible to set the external recycle flow to control the external syngas $H_2$:CO ratio in the normal operating or line-out range between 1.90:1 and 1.95:1.

i) The remainder of the catalyst can be added at the full reactor operating conditions since the internal and external recycle ratios and syngas $H_2$:CO ratio can be set so that even if 100% hydrogen conversion is attained the CO partial pressure will be above 0.5 bar (50 kPa) and the $H_2O$ partial pressure will be below 5 bar (500 kPa). A typical internal recycle gas to syngas ratio is between 0.8:1 and 1.2:1. A typical external recycle to natural gas ratio is between 0.2:1 and 0.4:1.

What is claimed is:

1. A process for starting up a slurry phase Fischer-Tropsch reactor, which process includes:

establishing, in a slurry phase Fischer-Tropsch reactor, an initial charge of molten wax, with an initial reactor temperature which is below the line-out reactor temperature but sufficiently high for a Fischer-Tropsch reaction to take place, and with the reactor containing, in contact with the molten wax, a partial catalyst inventory which is less than its line-out catalyst inventory;

feeding syngas into the reactor at an initial flow rate below the line-out syngas flow rate;

initially maintaining a syngas $H_2$:CO molar ratio at a value higher than 2:1;

thereafter decreasing the syngas $H_2$:CO molar ratio to its line-out value which is between 1:1 and 2:1; and increasing the syngas flow rate and the reactor temperature to their line-out values.

2. A process according to claim 1, wherein the syngas is that obtained by reforming natural gas in a reforming stage ahead of the Fischer-Tropsch reactor, with the decrease in the syngas $H_2$:CO molar ratio being effected by recycling carbon dioxide-containing gas to the reforming stage.

3. A process according to claim 2, wherein the carbon dioxide-containing gas that is recycled to the reforming stage is a tail gas from the Fischer-Tropsch reactor, with the process thus employing an external recycle system and the syngas that is fed into the reactor comprising reformed natural gas and reformed external recycle gas.

4. A process according to claim 1, wherein the Fischer-Tropsch catalyst is a supported cobalt catalyst.

5. A process according to claim 4, wherein the initial reactor temperature is between 180° C. and 200° C., while the line-out reactor temperature is between 220° C. and 260° C.

6. A process according to claim 4, wherein the initial syngas flow rate is from 30% to 70% of its line-out value.

7. A process according to claim 4, wherein the partial catalyst inventory comprises between 5% and 50% of the line-out catalyst inventory, and which includes, once the syngas $H_2$:CO molar ratio is at, or at least close to, its line-out value, adding further catalyst to the reactor to make up the line-out catalyst inventory.

8. A process according to claim 7, which includes
initially establishing, in the reactor, a charge of molten clean wax containing substantially no catalyst particles;
maintaining the charge of molten clean wax at a temperature above 150° C. and below 180° C.;
providing a slurry of molten wax and catalyst particles in a loading vessel;
transferring the slurry of molten wax and catalyst particles from the loading vessel to the reactor, where it is mixed with the charge of molten clean wax; and thereafter
raising the temperature in the reactor to the initial reactor temperature.

9. A process according to claim 8, which includes, while the reactor contains the charge of molten clean wax, recycling syngas that has passed through the reactor, after cooling and compression thereof, to the reactor, with the recycled syngas thus constituting an internal recycle and passing through the reactor in substantially unreacted form since the reactor temperature is below 180° C. and the reactor contains no catalyst, and with no external syngas then entering the reactor.

10. A process according to claim 9, wherein the flow rate of the syngas in the internal recycle is sufficient to fully fluidize the catalyst in the slurry in the reactor, prior to initiation of the Fischer-Tropsch reaction.

11. A process according to claim 9, wherein the catalyst particles are initially in the form of wax coated catalyst particles, with the slurry being provided in the loading vessel by adding the wax coated catalyst particles to the loading vessel, and thereafter heating the loading vessel to melt the wax which coats the catalyst particles, thereby forming the slurry of molten wax and catalyst particles.

12. A process according to claim 9, which includes pressurizing the loading vessel to a pressure which is about 200 kPa above the pressure in the Fischer-Tropsch reactor, so that the slurry is transferred from the loading vessel to the Fischer-Tropsch reactor by pressure differential.

13. A process according to claim 12, wherein the loading vessel is heated to a temperature above 150° C. before the pressure within the loading vessel is increased to above 100 kPa using a gas containing carbon monoxide.

14. A process according to claim 9, wherein the entire partial catalyst inventory is added to the reactor while syngas is recycled therethrough by means of the internal recycle, and while the reactor temperature is below 180° C.

15. A process according to claim 14, wherein the catalyst is added to the reactor in increments until the entire partial catalyst inventory has been reached.

16. A process according to claim 14, wherein after the entire partial catalyst inventory has been added to the reactor, the feeding of external syngas into the reactor is commenced.

\* \* \* \* \*